United States Patent
Lv et al.

(10) Patent No.: US 10,624,681 B2
(45) Date of Patent: Apr. 21, 2020

(54) INTERSPINOUS PROCESS BRACING SYSTEM

(71) Applicant: Ningbo Hicren Biotechnology Co., LTD, Ningbo, Zhejiang (CN)

(72) Inventors: Shiwen Lv, Ningbo (CN); Keya Mao, Ningbo (CN); Dongbing Feng, Ningbo (CN); Qingshan Zhuo, Ningbo (CN); Yu Wang, Ningbo (CN)

(73) Assignee: Ningbo Hicren Biotechnology Co., LTD, Ningbo, Zhejiang (CN)

( * ) Notice: Subject to any disclaimer, the term of this patent is extended or adjusted under 35 U.S.C. 154(b) by 0 days.

(21) Appl. No.: 16/062,552

(22) PCT Filed: Oct. 31, 2016

(86) PCT No.: PCT/CN2016/103990
§ 371 (c)(1),
(2) Date: Jun. 14, 2018

(87) PCT Pub. No.: WO2017/101599
PCT Pub. Date: Jun. 22, 2017

(65) Prior Publication Data
US 2019/0000514 A1    Jan. 3, 2019

(30) Foreign Application Priority Data
Dec. 15, 2015   (CN) .......................... 2015 1 0929128

(51) Int. Cl.
*A61B 17/70* (2006.01)
*A61B 17/00* (2006.01)

(52) U.S. Cl.
CPC .......... *A61B 17/7065* (2013.01); *A61B 17/70* (2013.01); *A61B 2017/00557* (2013.01)

(58) Field of Classification Search
CPC ........ A61F 2/4405; A61F 2/441; A61F 2/442; A61B 2017/00557; A61B 2017/0256;
(Continued)

(56) References Cited

U.S. PATENT DOCUMENTS 7,442,208 B2 * 10/2008 Mathieu ............. A61B 17/7068
623/17.11
8,034,080 B2 * 10/2011 Malandain ........... A61B 17/025
606/249

(Continued)

FOREIGN PATENT DOCUMENTS

CN   1545398   11/2004
CN   101155553   4/2008
(Continued)

OTHER PUBLICATIONS

International Search Report for PCT/CN2016/103990 dated Feb. 3, 2017, 6 pages.

*Primary Examiner* — Pedro Philogene
(74) *Attorney, Agent, or Firm* — Sheppard Mullin Richter & Hampton LLP (57) ABSTRACT

An interspinous process bracing system comprises an interspinous process brace and a delivery device. The interspinous process brace includes a flexible and foldable bag, and a filler. An injection opening is provided at a proximal end of the bag. The delivery device comprises a delivery tube. A distal end of the delivery tube is detachably connected to the injection opening. The filler can be injected, through the delivery tube and the injection opening, into the bag to expand the bag, forming the interspinous process brace. The system achieves interspinous process bracing through a minimally invasive surgery and thereby reduces injuries.

10 Claims, 9 Drawing Sheets

(58) Field of Classification Search
CPC ............ A61B 17/7065; A61B 17/7062; A61B
17/7067; A61B 17/7077; A61B 17/7068;
A61B 17/025; A61B 17/8863; A61B
17/1604; A61B 17/1608; A61B 17/1671;
A61B 17/1757; A61B 17/7047
USPC .............................. 606/246–279, 92–96, 99;
623/17.11–17.16
See application file for complete search history.

(56) References Cited

U.S. PATENT DOCUMENTS

| | | | |
|---|---|---|---|
| 9,603,714 B2* | 3/2017 | Kitagawa | A61F 2/442 |
| 9,936,988 B2* | 4/2018 | Davis | A61B 17/7097 |
| 2008/0114454 A1 | 5/2008 | Peterman et al. | |
| 2009/0118833 A1* | 5/2009 | Hudgins | A61B 17/7065 |
| | | | 623/17.16 |
| 2016/0302837 A1* | 10/2016 | Lv | A61B 17/7098 |

FOREIGN PATENT DOCUMENTS

| | | |
|---|---|---|
| CN | 103637842 | 3/2014 |
| CN | 103705322 | 4/2014 |
| CN | 104768484 | 7/2015 |
| CN | 105559868 | 5/2016 |

* cited by examiner

INTERSPINOUS PROCESS BRACING SYSTEM

CROSS REFERENCE TO RELATED APPLICATIONS

The present application is a national stage application of International Application PCT/CN2016/103990, filed Oct. 31, 2016, which claims the benefit of Chinese Patent Application No. 201510929128.0 filed Dec. 15, 2015, the contents of which are incorporated by reference in their entireties into the present disclosure.

TECHNICAL FIELD

The present invention relates to the field of medical device, more especially, to an interspinous process bracing system.

BACKGROUND

Lumbar instability is a common clinical disease, and early changes of lumbar are often caused by the internal structural disorder of the discus intervertebralis or the degenerative discogenic low back pains. With the development of the disease, vertebral bone hyperplasia, vertebral facet joint degeneration, and hypertrophy of ligamentum flavum will occur, which will lead to instability of the spine and spinal stenosis, along with mechanical pain of lumbar and symptom of lumbar spinal stenosis. When the conservative treatments fail, a surgery is often needed. The traditional surgical is fusion surgery, but studies have shown that it is not ideal through long-term clinical follow-up. As the fusion bracing destroys the biomechanical properties of the lumbar segments, the load transmission does not meet the original physiological conditions, thereby resulting in stress concentration and causing retrogression in the adjacent segments of the disc and in the vertebral facet joints.

The "non-fusion bracing" is the development trend of spine surgery in the future. "Non-fusion bracing" refers to a bracing method without fusion, which is implemented through changing the motion orientations and the load of the moveable lumbar segments, and which can control abnormal activities and allow physiological load transmission, thereby alleviating pains and effectively reducing the risks of accelerated degeneration of adjacent segments.

There are many types of non-fusion bracing, and most of the current researches relate to non-fusion interspinous process distractors. For example, the X-stop device described in the patent US20050075634A1 includes an elliptical central axis with a diameter of 10 mm at the middle segment and a length of 10 mm, and protuberant wings arranged at two ends thereof. The outer dimensions of the device are about 34.54×31.24×18.44 mm. The U.S. Pat. No. 6,946,000B2 describes a Wallis device, which comprises a band woven by two pieces of rough polyester and is fixed on a spacer made of Poly (ether ether ketone). The U.S. Pat. No. 5,645,599 describes a Coflex device, which consists of a U-shaped interspinous process spacer and four swings. The U.S. Pat. No. 6,626,944B1 describes a DIAM device, which is dumbbell-shaped and consists of a silicone externally applied polyethylene pipe.

However, in all the surgical methods mentioned in the relevant clinical documents, no matter the X-stop, the WAllis, the Coflex or the DIAM device, it is implanted through an open surgery, the procedure of which is complex and greatly increases the risks and pains of the patient. In addition, some interspinous process braces, such as In-space and Superion, can be implanted by minimally invasive procedures, but the incision is still greater than 2 cm.

Moreover, because its strength is far higher than that of the spinous process, the brace made of metal materials, such as the X-stop device, is likely to cause stress shielding and cause complications such as spinous process rupture.

SUMMARY

In view of the above defects of the prior art, the technical problem to be solved by the present invention is to provide a new interspinous process bracing system. The present invention aims at, through a minimally invasive surgery, delivering the new interspinous process brace to the interspinous process, then releasing the interspinous process brace, and injecting filler to brace the interspinous process. The present invention is in line with the development trend of the non-fusion bracing through a minimally invasive surgery, thereby achieving minimally invasive interventional treatments and reducing trauma to the patient.

The adopted technical schemes are as follows:

An interspinous process bracing system, comprises an interspinous process brace and a delivery device; the interspinous process brace includes a flexible and foldable bag and a filler; an injection opening is disposed at a proximal end of the bag; the delivery device includes a delivery tube; the injection opening is detachably connected with a distal end of the delivery tube; the filler is injected into the bag through the delivery tube and the injection opening to expand the bag, forming the interspinous process brace; a portion of the interspinous process brace, which is disposed between two spinous processes, forms a bracing segment; portions of the interspinous process brace, which protrude and are respectively disposed at two sides of the spinous processes, are configured to stop the interspinous process brace from moving between the spinous processes.

The objectives of the present invention can be realized through the following technical schemes:

Preferably, the bracing segment of the bag is provided with elastic gaskets, which is configured to brace elastically.

Preferably, the interspinous process bracing system is provided with a positioning marker, which is provided on the bag or on the delivery device, and which is configured to position the bracing segment of the bag.

Preferably, the positioning marker is arranged in an interlayer or on an outer surface of the bag.

Preferably, the delivery device further includes a protective sleeve; the protective sleeve is sleeved on the delivery pipe; during delivering the interspinous process brace, the delivery pipe slides along the protective sleeve; and the bag is folded and arranged at a distal end of the protective sleeve.

More preferably, a pre-shaped bracket is provided inside the bag; the pre-shaped bracket is fixedly connected with the bag; during delivering the interspinous process brace, the pre-shaped bracket is bar-shaped; when the bag comes out from the delivery device, the pre-shaped bracket rebounds and is positioned between the bracing segment of the bag and the spinous processes.

More preferably, the delivery device comprises a lining core; a lining tube is arranged inside the bag; a distal end of the lining tube is closed; the lining tube is fixed at a distal end of the bag; during delivering the interspinous process brace, the lining core is inserted into the delivery tube; a distal end of the lining core goes through the injection opening, extends into the bag, and is inserted into the lining tube to press against the distal end of the lining tube.

In one of the embodiments, an X-shaped positioning marker is provided at the distal end of the lining core and/or at the distal end of the protective sleeve; the X-shaped positioning marker is positioned corresponding to the bracing segment of the bag.

In one of the embodiments, the bag is provided with an axial position limiting structure; two ends of the axial position limiting structure are connected with two ends of the bag respectively.

In one of the embodiments, a length of the axial position limiting structure is less than a length of the bag in a natural stretch.

In one of the embodiments, the axial position limiting structure is disposed inside the bag.

In one of the embodiments, the axial position limiting structure comprises a position limiting tube; filling ports for filler are disposed in a tube wall of the position limiting tube; a distal end of the position limiting tube is fixed at the distal end of the bag, and a proximal end of the position limiting tube is connected to the injection opening; the lining core is inserted into the position limiting tube.

In one of the embodiments, the position limiting tube is a rigid tube or a flexible tube.

In one of the embodiments, the axial position limiting structure comprises position limiting wires; the position limiting wires are connected with two ends of the bag respectively.

In one of the embodiments, the axial position limiting structure is disposed on a surface or in the interlayer of the bag.

In one of the embodiments, a height of the bracing segment is above 4 mm.

In one of the embodiments, the injection opening is provided with a check valve.

Compared with the prior art, the present invention has beneficial effects as follows:

1. The working principle of the interspinous process bracing system of the present invention is as follows: firstly, implant a bag between the spinous processes through a delivery device; then inject the filler into the bag to expand the bag, forming the interspinous process brace and realizing interspinous process non-fusion bracing. Currently, there are no similar technical solutions in the field of interspinous process bracing through a minimally invasive surgery.

2. The interspinous process bracing system of the present invention implants the interspinous process brace through a minimally invasive surgery.

3. The interspinous process bracing system of the present invention can achieve less trauma, and the incision can be controlled to be less than 1 cm, while in the existing treatment schemes for spinous processes bracing at home and abroad, the incisions are all greater than 1 cm.

4. In terms of the height of the bracing segment, the existing interspinous process brace is generally divided into five specifications: 8, 10, 12, 14 and 16 mm. The interspinous process bracing system of the present invention adjusts the height of the bracing segment by controlling the injection amount of the filler, thereby realizing stepless heightening.

5. Most of the existing interspinous process braces are made of hard materials such as titanium alloy or PEEK. Before being implanted, the brace is in a fixed shape, so some tissues need to be cut or removed during the surgery, so as to match the shape of the brace. The interspinous process brace of the present invention comprises the bag and the filler. When the filler is injected into the bag and expands the bag, the outer contour of the brace matches with the shape of the spinous process, thereby achieving a perfect match with the physiological structure of the spinous process and better realizing the interspinous process bracing.

6. Regarding the interspinous process bracing system of the present invention, during the surgery, the ligament on the spinous process is not peeled, the hard tissues of the spinous process is not destroyed, and the original tissues around the spinous process are substantially retained, which is more beneficial to the recovery of the patient.

7. In the present invention, a check valve is arranged at the injection opening of the bag of the interspinous process brace. If the interspinous process brace needs to be repaired or taken out, the filler can be taken out first, which is simple and convenient to operate.

8. The interspinous process brace of the present invention is provided with elastic gaskets, which can not only realize bracing and fixing the spinous processes, but also preserve the motion degree of the hypsokinesis of the spine, thereby reducing the damages to the spinous processes.

9. The interspinous process brace of the present invention is provided with a positioning marker on the bag and on the delivery device, which can assist the doctor to position the interspinous process brace in the minimally invasive interventional operation, thereby improving the success rate of the surgery.

10. The interspinous process brace of the present invention is provided with an axial position limiting structure, which can optimize the shape of the brace expanded and brace the spinous processes effectively.

DESCRIPTION OF DRAWINGS

In order to make the content of the present invention more clear and better understood, the present disclosure will be further described in more details with reference to the accompanying figures and embodiments, wherein.

wherein: 100—bag; 1001—dumbbell-shaped bag; 1002—bag with two wings at only one side; 1003—straight cylinder-shaped bag without wing; 1004—bag with a respective wing at both sides; 110—injection opening; 120—pre-shaped bracket; 1201—X-pre-shaped bracket; 1202—Lantern-pre-shaped bracket; 1203—annular-pre-shaped bracket; 1204—double U-pre-shaped bracket; 1205—umbrella pre-shaped bracket; 130—elastic gasket; 140—positioning metal wire or sheet; 150—lining tube; 160—position limiting tube; 170—position limiting wire; 200—filler; 310—delivery tube; 320—lining core; 3201—X-shaped groove positioning marker; 330—protective sleeve; 340—threaded connection; 3401—threaded joint.

DETAILED DESCRIPTION OF DISCLOSED EMBODIMENTS

In order to make the objectives, technical schemes and advantages of the present disclosure more apparent and better understood, the present disclosure will be described in more details with reference to the accompanying figures and embodiments.

The proximal end as described in the present disclosure refers to the end near to the surgical operator, and the distal end refers to the end far away from the surgical operator.

Figure 1:
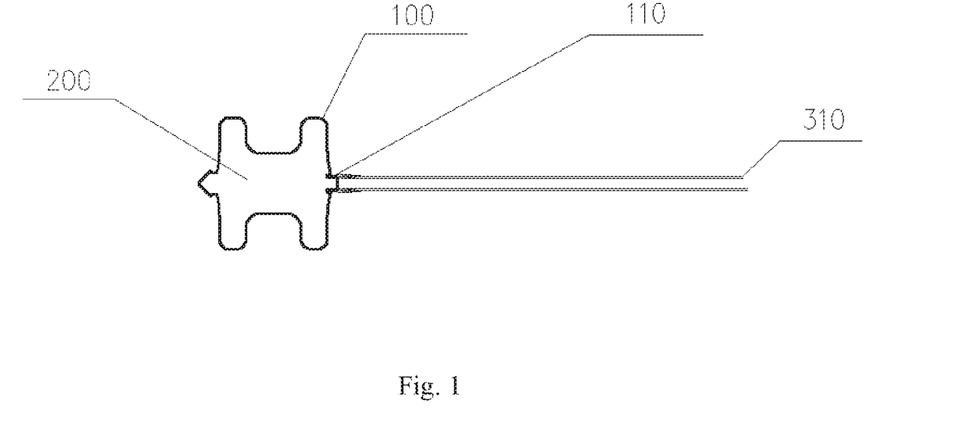
FIG. 1 is a schematic view illustrating an overall structure of an interspinous process bracing system according to the present invention.
Figure 2A:
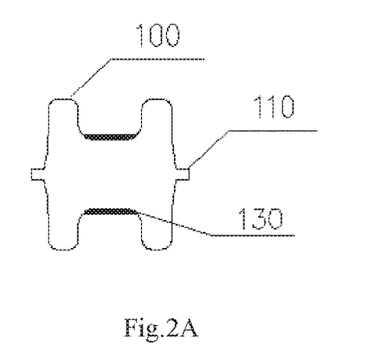
FIG. 2A is a schematic structural view of a bag with elastic gaskets in the present invention.
Figure 2B:
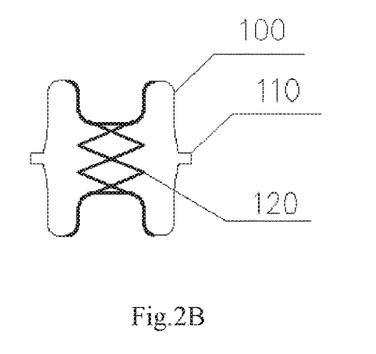
FIG. 2B is a schematic structural view of a bag with a pre-shaped bracket in the present invention; wherein, the pre-shaped bracket is fixedly connected with the bag.
Figure 2C:
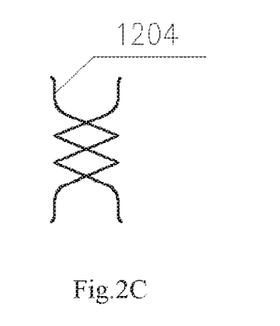
FIG. 2C is a schematic structural view of a U-pre-shaped bracket in the present invention.
Figure 2D:
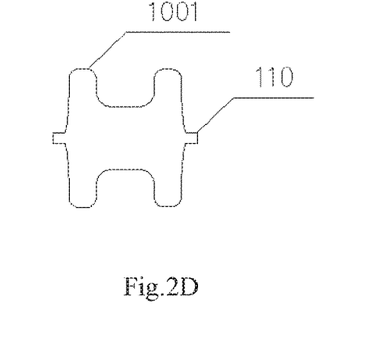
FIG. 2D is a schematic structural view of a dumbbell-pre-shaped bag in the present invention.
Figure 5A:
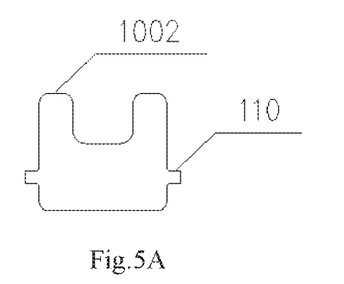
FIG. 5A is a schematic structural view of the bag with two wings at only one side in the present invention.
Figure 5B:
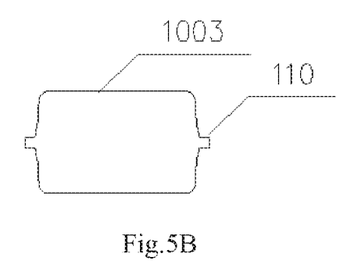
FIG. 5B is a schematic structural view of the straight cylinder-shaped bag without wing in the present invention.
Figure 5C:
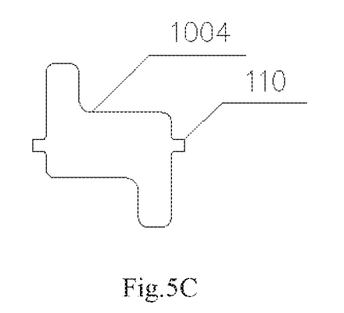
FIG. 5C is a schematic structural view of the bag with a respective wing at both sides in the present invention.
Figure 5D:
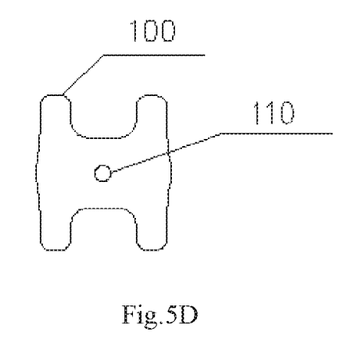
FIG. 5D is a schematic structural view of the bag with an injection opening disposed in the bracing segment in the present invention.
Figure 6A:
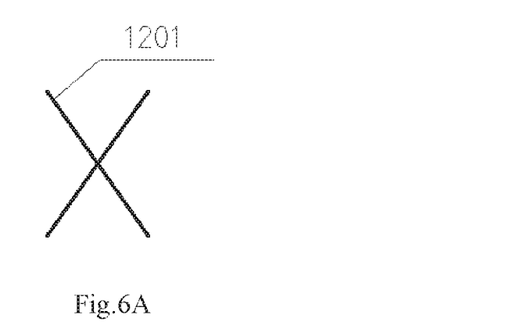
FIG. 6A is a schematic structural view of an X-pre-shaped bracket in the present invention.
Figure 6B:
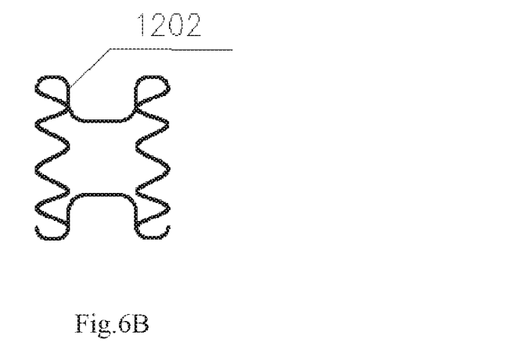
FIG. 6B is a schematic structural view of a lantern-pre-shaped bracket in the present invention.
Figure 6C:
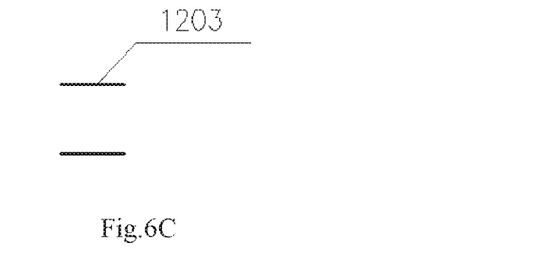
FIG. 6C is a schematic structural view of an annular-pre-shaped bracket in the present invention.
Figure 6D:
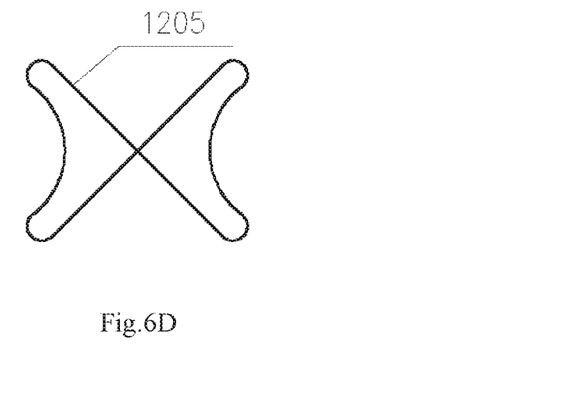
FIG. 6D is a schematic structural view of an umbrella-pre-shaped bracket in the present invention.

As shown in FIGS. 1 and 5D, a new interspinous process bracing system includes an interspinous process brace and a delivery device. The interspinous process brace includes a flexible and foldable bag 100 and a filler 200. An injection opening 110 is disposed at a proximal end of the bag 100. The delivery device includes a delivery tube 310. The injection opening 110 is detachably connected with a distal end of the delivery tube 310. The filler 200 is injected into the bag through the delivery tube 310 and the injection opening 110 to expand the bag 100, forming the interspinous process brace.

As shown in FIGS. 2A-2D, the bracing segment of the bag 100 is provided with elastic gaskets 130. The elastic gaskets 130 are disposed on the upper bracing surface and the lower bracing surface of the bracing segment of the bag, taking effects of bracing elastically. The bag 100 is provided with a positioning marker, and the positioning marker is a pre-shaped bracket 120, which is fixedly connected with the bag 100. The pre-shaped bracket 120 is a bracket 1204 with a double U-pre-shaped cross section, and the bag 100 is a dumbbell-shaped bag 1001. The injection opening 110 of the bag 100 is disposed at the proximal end of the bag 100.

Figure 3A:
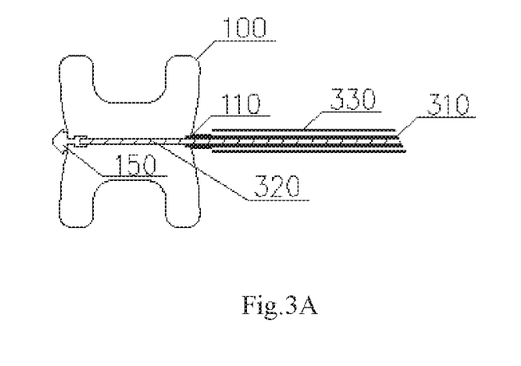
FIG. 3A is a schematic structural view of a bag with a lining core in the present invention.
Figure 3B:
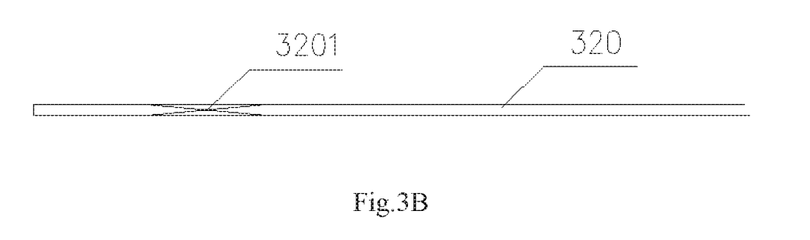
FIG. 3B is a schematic structural view of the lining core with an X-shaped groove in the present invention.
Figure 4A:
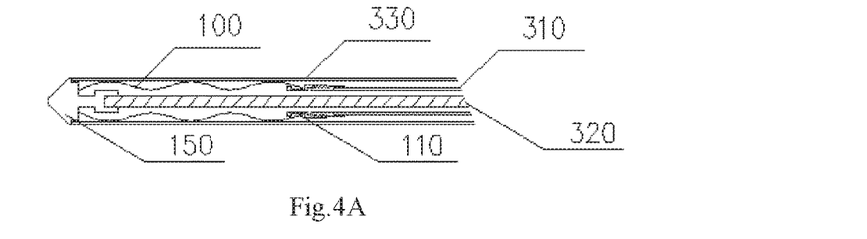
FIG. 4A is a schematic structural view of a bag folded and constricted in a delivery device in the present invention.
Figure 4B:
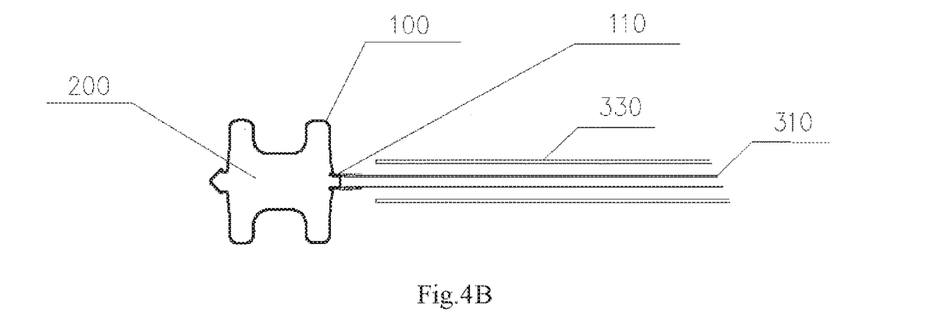
FIG. 4B is a schematic structural view of the bag exposed after the protective sleeve of the delivery device is withdrawn in the present invention.
Figure 4C:
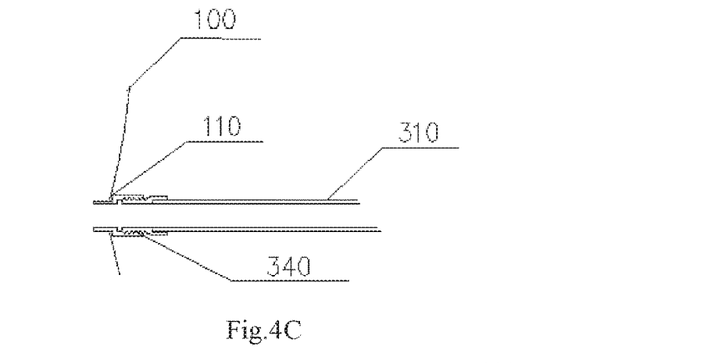
FIG. 4C is a schematic structural view of a detachable thread connection in the present invention.
Figure 4D:
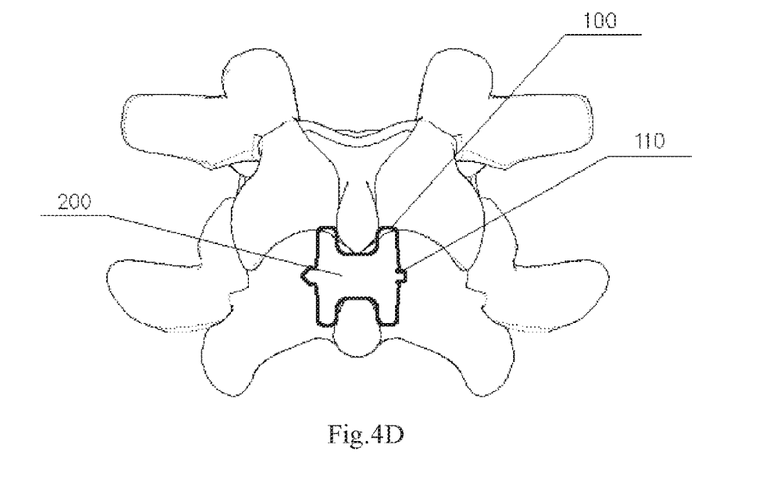
FIG. 4D is a schematic diagram illustrating the bracing effect of the interspinous process brace after the delivery device is withdrawn in the present invention.

As shown in FIGS. 3A-3B, a lining tube 150 is connected with the distal end of the bag 100, and a distal end of the lining tube 150 is closed. A lining core 320 is inserted into the delivery tube 310 slidably. A distal end of the lining core 320 is inserted into the blind hole of the lining tube 150 to press against the lining tube 150. The lining core 320 is a metal shaft, and a positioning marker is provided at the distal end of the lining core 320. The positioning marker is positioned corresponding to the bracing segment of the bag 100, and the positioning marker is an X-shaped groove 3201.

As shown in FIGS. 4A-4D, the delivery device further includes a protective sleeve 330. The protective sleeve 330 is sleeved on the delivery pipe 310 and can slide relative to the delivery pipe 310. The bag 100 is folded and constricted in the distal end of the protective sleeve 330. When the delivery device is operated, the protective sleeve 330 axially moves toward the proximal end of the delivery tube 310, and the bag 100 is exposed. The detachable connection between the injection opening 110 and the delivery tube 310 is a threaded connection 340. During the operation, the tiller 200 is injected into the bag 100 through the delivery tube 310 and the injection opening 110, expanding the bag 100 and forming the interspinous process brace. A portion of the interspinous process brace, which is disposed between two spinous processes, forms the bracing segment; portions of the interspinous process brace, which protrude and are respectively disposed at two sides of the spinous processes, stop the interspinous process brace moving between the spinous processes. The height of the bracing segment is not less than 4 mm, and the protruding portion is 2 mm higher than the bracing segment. The filler 200 does not overflow the bag 100 during the injection process, and the support strength of the interspinous process brace reaches 70 MPA. After the delivery device is withdrawn, the interspinous process non-fusion bracing is finished.

As shown in FIGS. 5A-5C, the bag 100 may also be a bag 1002 with two wings at only one side, a straight cylinder-shaped bag 1003 without wing, or a bag 1004 with one wing at both sides.

As shown in FIGS. 6A-6D, according to the shape of the cross section, the pre-shaped bracket 120 may also be an X-pre-shaped bracket 1201, a lantern-pre-shaped bracket 1202, an annular-pre-shaped bracket 1203, or an umbrella pre-shaped bracket 1205.

Figure 7:
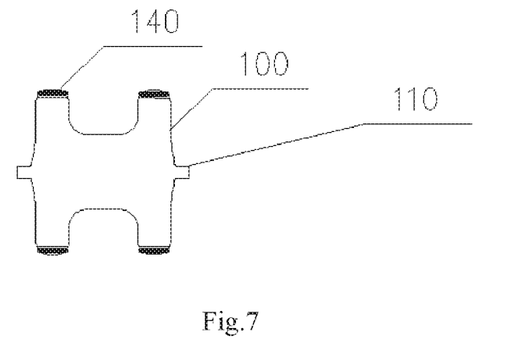
FIG. 7 is a schematic structural view of the bag provided with a positioning metal wire or sheet in the present invention.

As shown in FIG. 7, the bag 100 is provided with a positioning marker. The positioning marker comprises positioning metal wires or sheets 140 fixed in an interlayer or on an outer surface of the bag. The positioning metal wires or sheets 140 are axially and symmetrically distributed on the bag 100.

Figure 8:
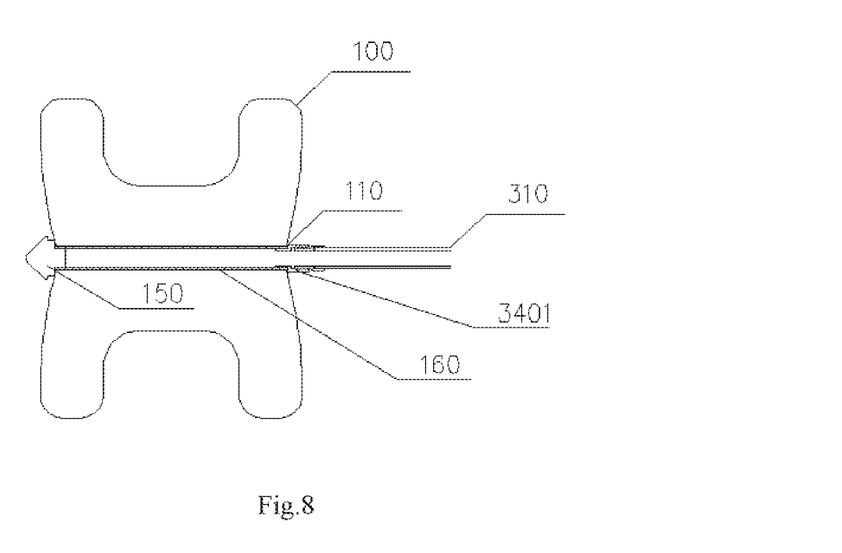
FIG. 8 is a schematic structural view of the bag with an axially position limiting structure which is embodied as a position limiting tube in the present invention.

As shown in FIG. 8, the bag 100 is provided with an axial position limiting structure. A lining tube 150 is arranged and connected at the distal end of the bag 100, a threaded joint 3401 is arranged and connected at the injection opening 110 disposed at the proximal end of the bag. The lining tube 150 is connected to the threaded joint 3401 through a position limiting tube 160. The position limiting tube 160 is arranged inside the bag 100 and has filling ports in its tube wall. The length of the position limiting tube 160 is less than the length of the bag 100 in a natural stretch. The position limiting tube 160 may be a rigid tube or a flexible tube. The lining tube 150 and the threaded joint 3401 are made of metal and may serve as positioning markers to identify the position of the bag 100.

Wherein, the length of the axial position limiting structure is less than the length of the bag 100 in a natural stretch. In addition, the axial position limiting structure may be arranged inside the bag 100.

The axial position limiting structure includes a position limiting tube 160. Filling ports for filler are disposed in a tube wall of the position limiting tube 160. The distal end of the position limiting tube 160 is fixed at the distal end of the bag 100, and the proximal end of the position limiting tube 160 is connected to the injection opening 110. The lining core 320 is inserted into the position limiting tube 160.

The position limiting tube 160 may be a rigid tube or a flexible tube.

Figure 9:
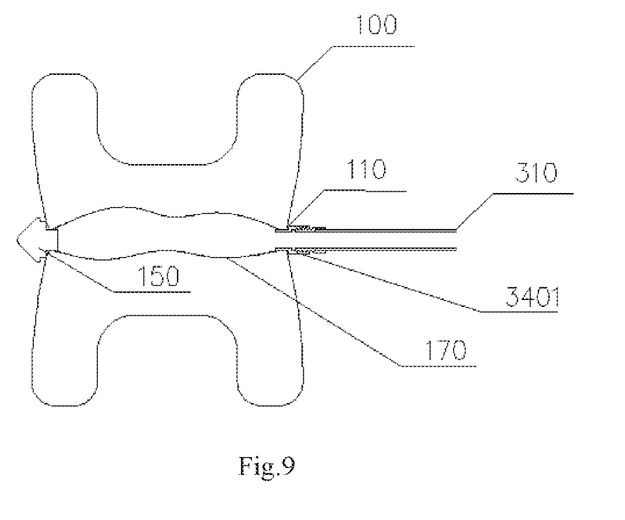
FIG. 9 is a schematic structural view of the bag with an axially position limiting structure which is embodied as a position limiting wire in the present invention.

The axial position limiting structure comprises position limiting wires 170. The position limiting wires 170 are connected with two ends of the bag 100 respectively.

As shown in FIG. 9, the bag 100 is provided with an axial position limiting structure. That is to say, a lining tube 150 is arranged and connected at the distal end of the bag 100, a threaded joint 3401 is arranged and connected at the injection opening 110 disposed at the proximal end of the bag. The lining tube 150 is connected to the threaded joint 3401 through two position limiting wires 170. The position limiting wires 170 are disposed inside the bag 100.

It is obvious that the above mentioned are only preferred embodiments of the present invention, but not intended to limit the embodiments of the present invention. It should be understood by the skilled in the art that various modifications and improvements can be made based on the description above. There is no need and no possibility to illustrate all embodiments, and all obvious modifications and improvements made on the basis of the present disclosure should be included in the protection scope of the present invention.

What is claimed is:

1. An interspinous process bracing system, comprising:
    an interspinous process brace and a delivery device, the interspinous process brace comprising:
        a flexible and foldable bag comprising:
            an injection opening at a proximal end;
            a structure disposed inside the bag and comprising a tube, the tube comprising:
                filling ports along a wall;
                a distal end attached to a distal end of the bag;
                a proximal end attached to the injection opening; and
                a lining core in an interior of the tube; and
            a filler disposed inside the bag and configured to expand the bag compared to a state in which no filler is disposed inside the bag; and
    the delivery device comprising a delivery tube comprising a distal end detachably connected with the injection opening,
    wherein:
        a portion of the interspinous process brace, when disposed between spinous processes, forms a bracing segment; protruding portions of the interspinous process brace disposed at opposite sides of the spinous processes are configured to stop the interspinous process brace from moving between the spinous processes; and
        the filler enters the bag through the delivery tube, the injection opening, and the filling ports.

2. The interspinous process bracing system according to claim 1, wherein, the bracing segment further comprises elastic gaskets, configured to elastically brace the bag.

3. The interspinous process bracing system according to claim 1, further comprising a positioning marker disposed on the bag or on the delivery device, the positioning marker being configured to position the bracing segment.

4. The interspinous process bracing system according to claim 3, wherein, the positioning marker is disposed in an interlayer or on an outer surface of the bag.

5. The interspinous process bracing system according to claim 1, wherein:
    the delivery device further includes a protective sleeve disposed on the delivery tube;
    during a delivery of the interspinous process brace, the delivery tube slides along the protective sleeve; and
    the bag is folded and disposed at a distal end of the protective sleeve.

6. The interspinous process bracing system according to claim 5, wherein:
    the bag further comprises a pre-shaped bracket fixedly connected with the bag and disposed inside the bag;
    during the delivery of the interspinous process brace, the pre-shaped bracket is bar-shaped; and
    when the bag comes out from the delivery device, the pre-shaped bracket rebounds and is positioned between the bracing segment and the spinous processes.

7. The interspinous process bracing system according to claim 5, wherein, the delivery device comprises:
    the lining core configured to be inserted into the delivery tube during the delivery of the interspinous process brace; and
    a lining tube disposed inside the bag, comprising a closed distal end that contacts a distal end of the lining core, and attached at the distal end of the bag, wherein:
        a distal end of the lining core goes through the injection opening, extends into the bag, and is inserted into the lining tube.

8. The interspinous process bracing system according to claim 7, further comprising:
    an X-shaped positioning marker at the distal end of the lining core or at the distal end of the protective sleeve, the X-shaped positioning marker being positioned corresponding to the bracing segment.

9. The interspinous process bracing system according to claim 1, wherein, a length of the structure is less than a length of the bag in a natural stretch position of the bag.

10. The interspinous process bracing system according to claim 1, wherein, the position limiting tube is a rigid tube or a flexible tube.

* * * * *